US008551555B2

(12) United States Patent
Burghard et al.

(10) Patent No.: US 8,551,555 B2
(45) Date of Patent: Oct. 8, 2013

(54) BIOCOMPATIBLE COATINGS FOR MEDICAL DEVICES

(75) Inventors: John Burghard, Vernonia, OR (US);
Carmen Campbell, Portland, OR (US);
Todd R. Younkin, Portland, OR (US);
Markus Kuhn, Portland, OR (US);
David Shykind, Sherwood, OR (US);
Jose Maiz, Portland, OR (US)

(73) Assignee: Intel Corporation, Santa Clara, CA (US)

( * ) Notice: Subject to any disclaimer, the term of this patent is extended or adjusted under 35 U.S.C. 154(b) by 1064 days.

(21) Appl. No.: 11/964,428

(22) Filed: Dec. 26, 2007

(65) Prior Publication Data
US 2009/0169714 A1 Jul. 2, 2009

(51) Int. Cl.
*A61L 33/00* (2006.01)
(52) U.S. Cl.
USPC .......... 427/2.25; 427/459; 427/475; 427/482; 427/486; 118/630; 118/634
(58) Field of Classification Search
USPC .......... 427/2.1, 539, 255.6, 255.7, 409, 327, 427/2.15, 2.24, 2.25, 2.28, 2.3, 457, 458, 427/459, 466, 523, 581, 582, 585, 496, 488, 427/595, 596, 248.1, 255.5, 475, 482, 486; 623/1.11, 1.42; 600/36; 424/423
See application file for complete search history.

(56) References Cited

U.S. PATENT DOCUMENTS

| | | | | |
|---|---|---|---|---|
| 5,773,097 A * | 6/1998 | Rogari | | 427/459 |
| 6,368,658 B1 * | 4/2002 | Schwarz et al. | | 427/2.15 |
| 7,001,328 B1 * | 2/2006 | Barofsky et al. | | 600/36 |
| 2004/0098117 A1 * | 5/2004 | Hossainy et al. | | 623/1.42 |
| 2004/0208845 A1 * | 10/2004 | Michal et al. | | 424/78.24 |
| 2005/0220839 A1 * | 10/2005 | DeWitt et al. | | 424/423 |
| 2006/0047336 A1 * | 3/2006 | Gale et al. | | 623/1.11 |

OTHER PUBLICATIONS

Asami, K., et al., "An X-Ray Photo-Electron Spectroscopic Study of Surface Treatments of Stainless Steels", Corrosion Science, vol. 19, Pergamon Press Ltd., (1979), Great Britain, (pp. 1007-1017).
Bertrand, Olivier F., et al., "Biocompatibility Aspects of New Stent Technology", Journal American College of Cardiology, vol. 32, No. 3, Sep. 1998, Elsevier Science, Inc., (pp. 562-571).
Davis, Daniel H., et al., "Immobilization of RGD to <111> Silicon Surfaces for Enhanced Cell Adhesion and Proliferation", Biomaterials 23 (2002), Elsevier Science, Ltd. (USA), www.elsevier.com/locate/biomaterials, (pp. 4019-4027).
Hunter, William L., "Drug-Eluting Stents: Beyond the Hyperbole", Advanced Drug Delivery Review 58 (2006), Elsevier Science, Ltd. (USA), www.elsevier.com/locate/addr, available online at: www.sciencedirect.com, (pp. 347-349).

(Continued)

*Primary Examiner* — Dah-Wei Yuan
*Assistant Examiner* — Andrew Bowman

(57) ABSTRACT

Biocompatible coatings for implantable medical devices are disclosed. Embodiments of the invention provide methods for coating an object with a biocompatible coating wherein the device is suspended using a flowing gas during the coating process. Embodiments of the invention provide tropoelastin coatings and methods of creating tropoelastin coatings for implantable medical devices. Optionally, the biocompatible coating can be a drug eluting coating.

29 Claims, 9 Drawing Sheets

(56) References Cited

OTHER PUBLICATIONS

Kamath, Kalpana R., et al., "The Taxus Drug-Eluting Stent: A New Paradigm in Controlled Drug Delivery", Advanced Drug Delivery Reviews 58 (2006), Elsevier Science, Ltd. (USA), www/elsevier.com/locate/addr, available online at: www.sciencedirect.com, (pp. 412-436).

Kim, Jinmo, et al., "Protein Immobilization on Plasma-Polymerized Ethylenediamine-Coated Glass Slides", Analytical Biochemistry 313 (2003), Elsevier Science, Ltd. (USA), Academic Press, www.elsevier.com/locate/yabio, available online at: www.sciencedirect.com, (pp. 41-45).

Poncin, P., et al., "Comparing and Optimizing Co-Cr Tubing for Stent Applications", Materials & Processes for Medical Devices Conference, Aug. 25-27, 2004, ASM International, The Materials Information Society, (5 pages).

* cited by examiner

BIOCOMPATIBLE COATINGS FOR MEDICAL DEVICES

BACKGROUND OF THE INVENTION

Field of the Invention

The embodiments of the present invention relate generally to implantable medical devices and biocompatible coatings for medical devices.

BACKGROUND INFORMATION

In many instances, it is desirable to implant a device into a mammal for monitoring biological processes or reconstructing or repairing injured or diseased tissue or bone. The biocompatibility of the implanted bio-accessible surface is critical to the success of the implanted medical device. Metallic surfaces, such as SS 316L stainless steel commonly used in implantable medical devices such as cardiovascular stents, can elicit immune rejection which may include localized and systemic inflammatory responses and fever. In the specific case of stents, immune rejection may also result in restenosis (re-narrowing of the vessel wall) which progressively blocks the artery and requires renewed medical intervention to resolve the blockage. Additionally, available permanent intracoronary stents may also be complicated by thrombosis, or the localized coagulation of blood in the vicinity of the stent, causing restriction or blockage of the blood flow.

Coatings believed to improve the biocompatibility of implanted medical devices have been applied to bio-accessible surfaces. These coatings that are believed to have improved biocompatibility are sometimes combined with immunosuppressive drugs. This combination of coatings and immunosuppressive drugs improves somewhat the outlook for the patient but the incidence of device rejection related complications is still significant. However, coated medical devices have not entirely eliminated biocompatibility issues and many medical problems stemming from implanted devices are believed to be the result of defects and non uniformity in the biocompatible coating on the device.

DETAILED DESCRIPTION OF THE INVENTION

Figure 1:
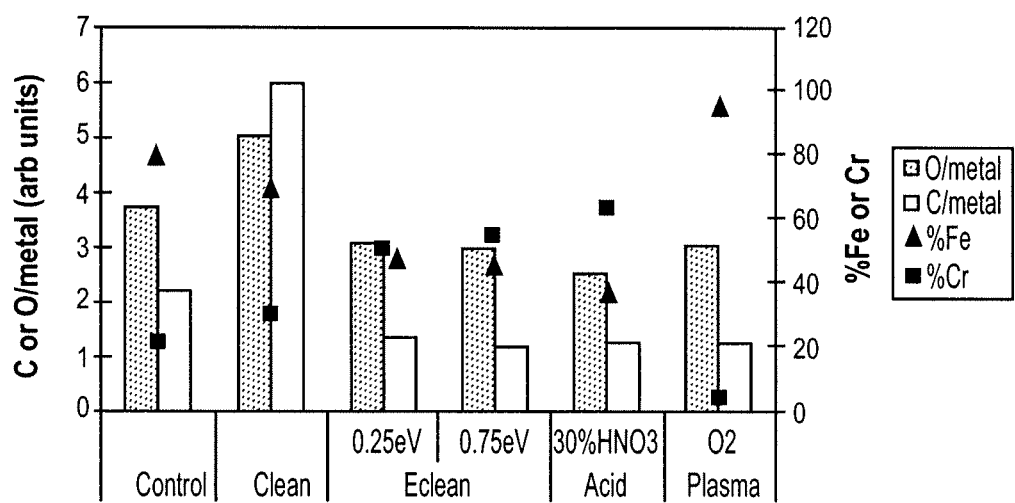
FIG. 1 provides the results of XPS (X-Ray Photoemission Spectroscopy) surface analysis of several SS 316L stainless steel surfaces that were prepared to receive a biocompatible coating according to several different procedures.

Embodiments of the present invention provide bio-implantable devices, coatings, and methods for creating bio-implantable devices and bio-compatible coatings. In some embodiments a bio-compatible coating is created, in part, by using a bio-compatible protein, such as tropoelastin. Tropoelastin is an approximately 72-kDa soluble biosynthetic precursor to the protein elastin. In vertebrates, elastin is formed through the secretion and crosslinking of tropoelastin. The crosslinked elastic protein elastin is a component of elastic fibers in the extracellular matrix. In general, elastin is a fairly stable component of the extracellular matrix and it undergoes little post-developmental change or breakdown throughout the lifetime of a mammal. Elastin is relatively permanent component of connective tissue during the life of an organism. Tropoelastin has been used as a coating material for medical devices. For example, U.S. Pat. No. 7,001,328 and WO 1998/034563 describe the use of tropoelastin for producing biomaterials and bio-implantable devices.

Tropoelastin useful in the present invention can be, for example, isolated from mammalian tissue or produced from a recombinant expression system. Tropoelastin can also be produced from mammalian cell culture systems. Short term culture of bovine vascular endothelial cells, nuchal ligament fibroblasts from cows and sheep, human skin fibroblasts results in the accumulation of tropoelastin in the culture medium. Recombinant tropoelastin, such as human recombinant tropoelastin (hrTE), can be produced from a protein expression system. Using recombinant technology, cDNA encoding tropoelastin can be cloned and expressed in protein expression systems to produce biologically active tropoelastin. Functionally distinct hydrophobic domains and lysine rich crosslinking domains are encoded in exons within the tropoelastin gene. Multiple splice variants are found across species. Further, the peptide sequence of the naturally occurring tropoelastin can be altered through mutagenesis of the gene and the engineering of DNA sequence variants. Expression of the full length elastin cDNA clone, cHEL2 and purification of recombinant human tropoelastin was demonstrated, for example, by Rosenbloom, J., Abrams, W. R., and Mecham, R., *The FASEB Journal*, 7 (1993) 1208-1218.

In vivo, tropoelastin is crosslinked by several bi- and tetra-functional crosslinks (bifunctional lysinonor-leucine and allysine aldol, and tetrafunctional desmonsine crosslinks) to form elastin. These crosslinks are the product of the oxidative deamination and condensation of lysyl side chains in the tropoelastin polypeptide. In vitro, tropoelastin crosslinks can be formed, for example, through several different chemical routes. Tropoelastin can be crosslinked by the copper dependent enzyme lysyl oxidase, and the resulting crosslinked structure resembles the crosslinks found in natural elastin. Tropoelastin can also be crosslinked through the use of γ-radiation. Optionally, the tropoelastin may be γ-irradiated in the presence of sulfur derivatives. Further, tropoelastin may be crosslinked through the use of chemical crosslinking reagents such as, for example, glutaraldehyde, dimethylpimelidate, sulfosuccinimidyl maleimidomethyl cyclohexane carboxylate (SMCC), N-hydroxysulfosuccinimide (Sulfo-NHS), and disuccinimidyl suberate (DSS).

Optionally the tropoelastin monomers may be organized into a filamentous structure before crosslinking. Raising the temperature of an aqueous tropoelastin solution causes the tropoelastin monomers to aggregate into a filamentous structure called a coacervate. Coacervated tropoelastin can be crosslinked using lysyl oxidase to produce elastin fibrils.

Examples of implantable medical devices and medical devices and mechanical structures that may use a bio-compatible coating include, but are not limited to, stents, conduits, scaffolds, cardiac valve rings, cardiovascular valves, pacemakers, hip replacement devices, implanted sensor devices, esophageal stents, heart implants, bio-compatible linings for heart valves, dialysis equipment and oxygenator tubing for heart-lung by-pass systems. Exemplary implanted sensor devices include sensors for monitoring congestive heart failure that collect and provide cardiac pressure data.

In general, a stent is a device, typically tubular in shape, that is inserted into a lumen of the body, such as a blood vessel or duct, to prevent or counteract a localized flow constriction. The purpose of a stent, in some cases, is to mechanically prop open a bodily fluid conduit. Stents are often used to alleviate diminished blood flow to organs and extremities in order to maintain adequate delivery of oxygenated blood. The most common use of stents is in coronary arteries, but they are also widely used in other bodily conduits, such as, for example, central and peripheral arteries and veins, bile ducts, the esophagus, colon, trachea, large bronchi, ureters, and urethra. Frequently, stents inserted into a lumen are capable of being expanded after insertion or are self-expanding. For example, metal stents are deployed into an occluded artery using a balloon catheter and expanded to restore blood flow. For example, stainless steel wire mesh stents are commercially available from Boston Scientific, Natick, Mass.

Materials for implantable medical devices structures include, but are not limited to, stainless steel grade 316 (SS 316L) (comprised of Fe, less than 0.3% C, 16-18.5% Cr, 10-14% Ni, 2-3% Mo, less than 2% Mn, less than 1% Si, less than 0.45% P, and less than 0.03% S), tantalum, chromium molybdenum alloys, nickel-titanium alloys (such as nitinol) and cobalt chromium alloys (such as MP35N, ASTM Material Designation: 35Co-35Ni-20Cr-10Mo). Typical metals currently in use for stents, include SS 316L steel and MP35N. See also, "Comparing and Optimizing Co—Cr Tubing for Stent Applications," Poncin, P., Millet, C., Chevy, J., and Profit, J. L., Materials & Processes for Medical Devices Conference, August 2004, ASM International. The present invention is not limited to a particular material onto which a bio-compatible coating is formed, the underlying material used for the implantable medical device can be chosen according to a variety of factors, such as mechanical stability and ease of formation.

Implantable medical devices composed of metals such as stainless steel can elicit immune rejection responses upon implantation. These effects may include localized and systemic inflammatory response and fever. Although rejection can be mitigated by prescribing immunosuppressive drugs, systemic side effects of immunosuppressive drugs, which include immune deficiencies and infection, potentially limit their use. Immune mediated rejection effects may be attenuated by coating the implantable device with a biocompatible material and also by providing localized drug delivery by incorporating a drug into the implantable medical device. Types of drugs that can be used with stents or other implantable medical devices include, for example, antibiotics, immunosuppressive compounds, anti-inflammatories, anti-cell proliferation compounds, anticoagulants, antisense molecules, antivirals, anti-neoplastics, chemotherapeutics, and combinations thereof. For example, compounds that have been used with drug-eluting implantable medical devices include rapamycin (sirolimus), paclitaxel (taxol), Hirudin, Methatrexate, and zotarolimus, biolimus A9, dexamethasone, ABT-578, and tacrolimus.

Processes based on wet chemistry can be used to deposit biocompatible films. After cleaning with a detergent, electrochemical methods may be used for surface preparation followed by a surface silanization reaction that provides a surface onto which the biocompatible film can be adhered. In this process, the surface on which the bio-compatible film will be formed is sonicated in a detergent solution and prepared electrochemically by oxidizing it at 0.25 eV in a 0.5 M $H_2SO_4$ solution. This biocompatible film can be deposited in sequence with a crosslinking compound to make the film insoluble and suitable as a final coating surface. If desired, the film may then be exposed to a solution containing a drug that is absorbed into the crosslinked biocompatible film.

According to embodiments of the invention, a vacuum-based process is provided for creating a bio-compatible film surface. A metallic surface to be exposed to a bio-environment is cleaned in a vacuum chamber using an oxygen plasma (dry etch). The plasma etch procedure can be accomplished using a standard plasma processing chamber as used in semiconductor processing procedures, that typically is comprised of a chamber, a vacuum system, a gas supply system, and a power supply. In a typical etch process, the sample is placed in the chamber, the chamber is evacuated, and the chamber is filled with the reactive gas under reduced pressure. Plasma processing chambers ionize a variety of source gases in a vacuum system using RF (radio frequency) energy (usually 13.56 MHz) typically applied through electrodes in the processing chamber. The sample to be processed can be placed on a grounded electrode in the plasma chamber. Ionized particles in the plasma gas react with the sample surface. For example, the plasma chamber can be a Plasmalab µEtch 300 from Oxford Instruments, Oxfordshire, UK.

Advantages of the oxygen plasma include that the plasma can remove unwanted impurities and terminate the surface with an optimal chemistry toward further attachment of desired species. The use of a vacuum-based plasma surface preparation process avoids the possibility of micro-contaminants from a solution-based cleaning process being deposited on the surface. An exemplary plasma etch process for a medical device can be performed using oxygen gas ($O_2$) and an inert gas such as nitrogen ($N_2$), He, or Ar as a carrier gas. In general, plasma etch parameters that can be employed include $O_2$ flow rates of 45 to 55 sccm, Ar (or other inert carrier gas) flow rates of 4 to 6 sccm, chamber pressure of 50 to 250 Torr, and power levels of 300 to 800 W.

In alternate embodiments, ion beam etching (sputter milling or sputter etching) may be employed. Ion beam etching is a physical process in which a target (such as in this case, a medical device) is placed in a vacuum chamber and is bombarded with high energy ionized argon gas (Ar) that has been created by a stream of high-energy electrons. The positively charged high energy Ar is accelerated toward the target which is placed on a negatively charged electrode. The impact of Ar atoms dislodges surface material from the medical device.

In an alternate embodiment, the surface may be electrochemically cleaned using a solution of 0.5% $H_2SO_4$ and 30% $HNO_3$ by weight at 0.75 eV. XPS surface analysis of the resulting cleaned surface is provided in FIG. 1. XPS data was collected on a Thermo Fisher VG Scientific XPS 402, available from Thermo Scientific, Waltham, Mass. Data was collected using survey mode from 0-1200 eV in 1.0 eV steps and a pass energy of 400 eV to maximize sensitivity. The angle resolved detector was run in angle-integrated mode with angular collection from 23-83 degrees to the surface normal.

In FIG. 1, the native stent (as received), the stent after initial solvent cleaning, and the stent after the current process of cleaning the metal surface using 0.25 eV (in a solution of 0.5 M $H_2SO_4$) are compared to the stent after an improved wet chemical process using 0.75 eV (in a solution of 5 M $H_2SO_4$) for 1 minute, wet chemical oxidation at 0.75 eV with $HNO_3$ (in a solution of 0.5% $H_2SO_4$), and the stent surface after an $O_2$ plasma etch. The use of plasma processing leaves the stent surface rich in iron and diminished in chromium. In this example, the levels of carbon contamination appear to be similar for the plasma process and for the wet chemistry processes because the plasma processed samples were exposed to air prior to XPS analysis. Since the surface can be reacted with the silanating species in situ after the plasma processing (without exposure to the atmosphere), the carbon contamination can be attenuated.

Figure 2:
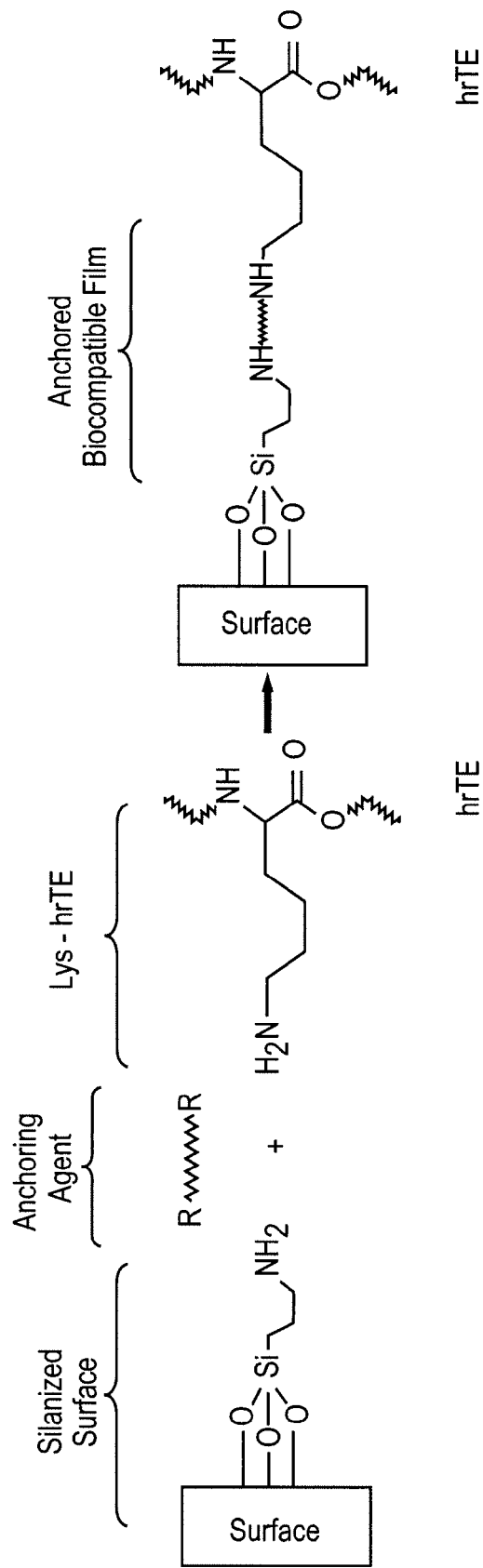
FIG. 2 diagrams a coupling reaction that attaches a biocompatible coating to the surface of a medical device.

Optionally, a thin layer of metal may be sputtered onto the surface of the medical device before and/or after the plasma clean cycle. Sputtering of a thin metal layer allows the surface of the medical device to be tailored for the subsequent adhesion of a biocompatible film. The ability to sputter a metal layer decouples the properties of the surface which may be optimized for adhesion or biocompatibility from the properties of the core materials of the device which may be optimized for different purposes, such as for mechanical robustness. Metals that may be sputtered onto the surface, include, but are not limited to, chromium, iron, cobalt, nickel, tantalum, titanium, gold, platinum, and aluminum, and mixtures thereof. In FIG. 2, the surface to be coated with a biocompatible film is reacted with a silanizing agent that is then used to couple the biocompatible film to the device surface. Optionally, the device surface may be reacted with a silanating species either through wet chemistry or through vacuum-based chemistry. In a wet chemical procedure, for example, the medical device is placed in a solution of silanating agent, such as aminopropyltriethoxysilane (APTS) in toluene, and allowed to react for 24 hours at room temperature. The device was then annealed at 120° C. for 10 minutes in an inert atmosphere ($N_2$). See also, "Immobilization of RGD to <111> Silicon Surfaces for Enhanced Cell Adhesion and Proliforation," Davis, H. D., Giannoulis, C. S., Johnson, R. W., Desai, T. A., *Biomaterials*, 23, 4019 (2002) and Hermanson, G. T.; Mallia, A. K.; Smith, P. K. *Immobilized Affinity Ligand Techniques*, Academic Press, Inc. (1992). A vacuum-based silanization procedure avoids having contaminants from the atmosphere deposited onto the surface after the plasma clean. For example, atmospheric organic contaminants readily resorb on to the surface following removal from plasma chamber. These surface contaminants interfere with the silanization reaction and prevent optimal completion of the reaction of the surface with the silanization species. In the vacuum-based process, the silane species is vaporized and deposited onto the surface of the device. Vapor deposition processes favor the formation of a monolayer of the silane species on a surface. The vacuum-based silanization process can be accomplished in the chamber in which a plasma etch was performed without exposing the etched surfaces to the atmosphere after etching. Alternately, the device may be transferred under vacuum or in an inert atmosphere to a second chamber for the vapor deposition of the silane species. The silane species may be heated to accomplish vaporization, placed under vacuum to achieve vaporization, or heated under vacuum, depending on the physical properties of the silane species selected. During this process, other inert gases may be present, such as $N_2$, helium, or argon gases. Maintaining the temperature of the substrate onto which the silane is deposited between about 50 and 120° C. promotes reaction of the silane species with the substrate surface. Reaction times are generally about 4 to about 24 hours. The device can then be heated to anneal the coating.

Figure 3:
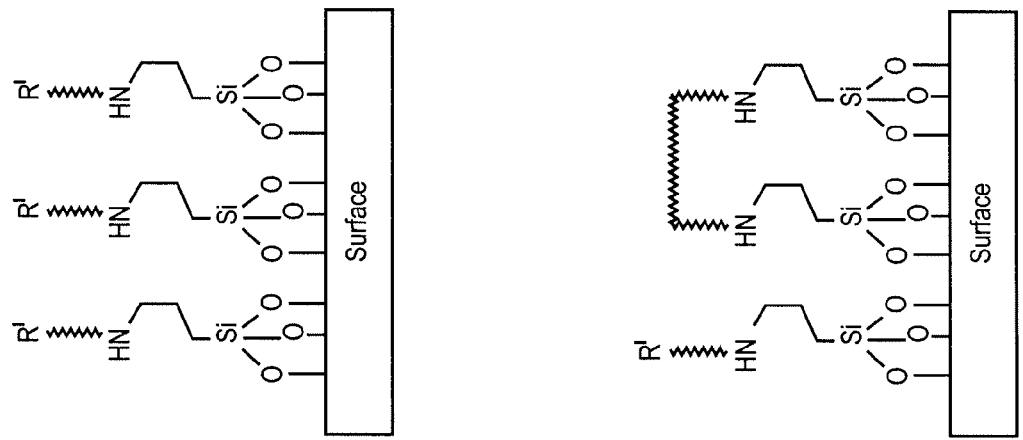
FIG. 3 shows an undesirable reaction that can occur between surface-attached species that interferes with the coupling of a biocompatible coating to the surface of a medical device.
Figure 3:
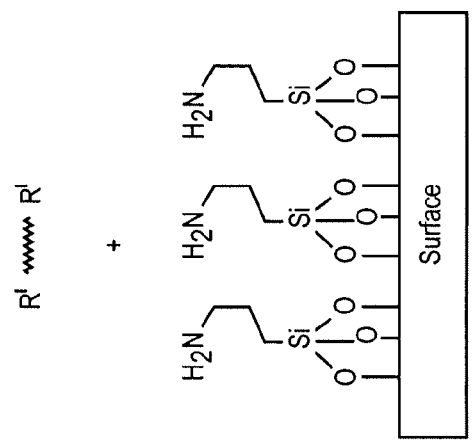
Figure 4:
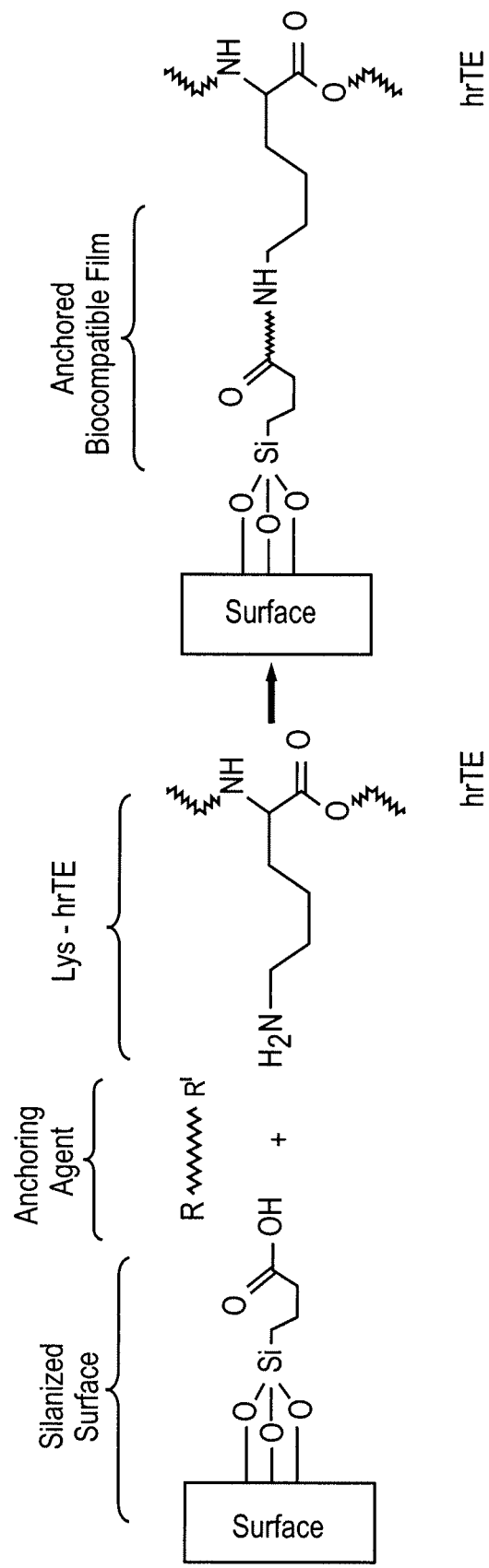
FIG. 4 diagrams a further coupling reaction that attaches a biocompatible coating to the surface of a medical device.

Optionally, the silanizing species provides a reactive organic group for coupling the biocompatible coating that is other than a primary amine functional group. As shown in FIG. 3, agents that couple amine groups from the biocompatible protein coating to the amine groups presented by the surface-attached silane also couple the silane amine groups to each other. The reaction between two anchoring agents leads to ineffective coupling between the silanized surface and the biocompatible film due to the absence of some of the surface-attached coupling sites. Having a surface-presented functional group other than an amine leads to better adhesion and better surface coverage by the biocompatible coating, and therefore increased biocompatibility of the implantable medical device. The organic group presented by the surface-attached silane molecule for coupling can be, for example, a carboxylic group, an aldehyde, an ester, an alkene, an alkyne, a thiol, an isocyanate, a substituted amine, an epoxide, or an alcohol. A typical silane that can be used to modify a surface toward further molecular attachment can be of the chemical formula, $X_3$—Si—YR", where X is a leaving group, such as for example, —Cl, —$OCH_3$, or —$OCH_2CH_3$, and R" is a reactive coupling group, such as for example, —$NH_2$, —COOH, —COH, —$CHCH_2$, and —SH (and others described herein). In general, Y is a hydrocarbon having from 1 to 10 carbon atoms. Examples of —YR" include, —$(CH_2)_3$ $NH_2$, —$(CH_2)_2COOH$, and —$(CH_2)_2SH$. Some exemplary silanes include, 3-aminopropyltriethoxysilane (APTS), mercaptosilane, and glycidoxytrimethoxysilane (having an epoxide reactive coupling group). Silanes having reactive coupling groups are commercially available from, for example, Gelest, Ltd., Kent, UK. FIG. 4 shows the coupling reaction between a carboxylic acid surface-attached functional group and a primary amine group, such as a lysine residue, from the biocompatible proteinaceous coating.

Figure 5:
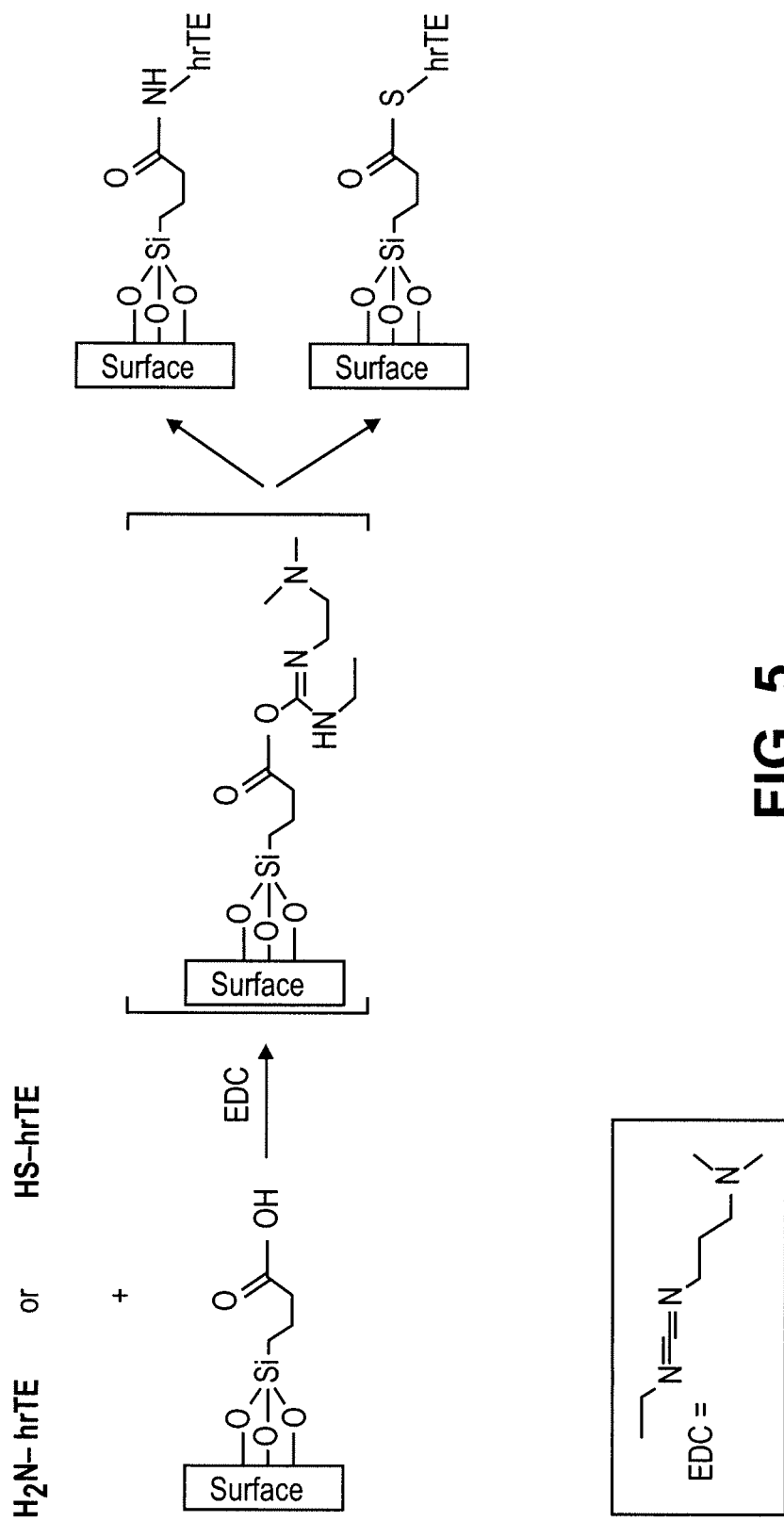
FIG. 5 diagrams a coupling reaction that can be used to attach a biocompatible coating to the surface of a medical device.

In general, the linker molecule, or anchoring agent, shown in FIGS. 2-5, is a bifunctional molecule that is capable of forming a chemical bond with the functional group presented by the surface-attached silane and a functional group from the biocompatible coating. For example, in FIG. 2, the R group could be an aldehyde and the linker molecule could be glutaraldehyde. The two functional groups, R and R or R and R', are joined together by an organic bridge that is from one atom in length to about 15 atoms in length. For example, the organic bridge could be a methyl-, ethyl-, or propyl-chain. The organic bridge could be comprised of atoms other than carbon, such as nitrogen, oxygen, or sulfur. The organic bridge could be substituted by organic functional groups, such as, for example, methyl- or hydroxyl-groups. In FIG. 4, the linker molecule is a bifunctional molecule that is capable of forming a chemical bond with the functional group presented by the surface-attached silane and a functional group from the biocompatible coating, wherein the groups R and R' are organic functional groups that are chemically different from each other. Ideally, if R is capable of forming a covalent bond with the functional group presented by the surface-attached silane, R' would not be capable of forming a covalent bond with the functional group presented by the surface-attached silane under similar reaction conditions. FIG. 5 provides a specific coupling reaction between a surface-attached carboxylic acid functional group and an amine group of a lysine residue or a thiol group of a cysteine residue from the biocompatible proteinaceous coating. In this case the linker molecule is 1-ethyl-3-(3-dimethylaminopropyl)-carbodiimide (EDC). Other coupling agents include N-Succinimidyl- 3-maleimidopropionate (SMP), thiophosgene, and dithionite. See for example, Davis, H. D., Giannoulis, C. S., Johnson, R. W., Desai, T. A., *Biomaterials,* 23, 4019 (2002). Methods for coupling proteins to surface-attached functional groups are known and can be found in Aslam, M. and Dent, A., *Bioconjugation: Protein Coupling Techniques for the Biomedical Sciences*, Grove's Dictionaries, Inc., 301-316 (1998), for example. Some representative examples of R and R' include, aldehydes, amines, carboxylic acids, and thiols. Attachment sites for a biocompatible protein coating include, for example, an amine or carboxy terminus of the protein, a lysine residue, an aspartic acid residue, a glutamic acid residue, or a cysteine residue.

A biocompatible proteinaceous coating can be applied to a medical device by dipping the device into a solution containing the biocompatible proteinaceous coating molecules and removing the device from the solution (dip coating). The device may then optionally be spun or centrifuged to remove excess proteinaceous coating. The device is then dipped into a solution containing a crosslinker and then optionally dipped into a solution containing a therapeutic agent. The process optionally may be repeated to build up a coating upon the surface.

Figure 6:
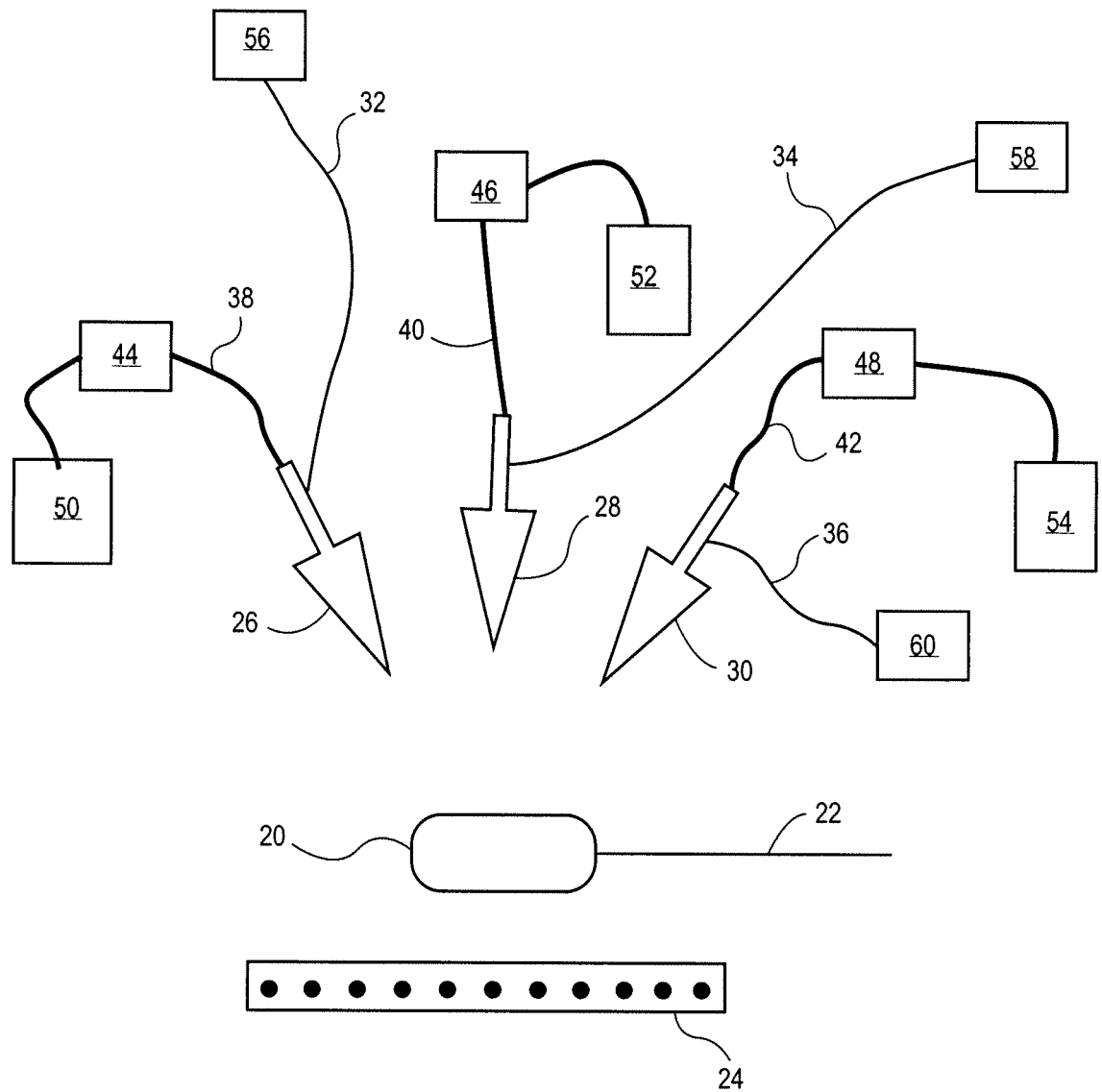
FIG. 6 diagrams a system for spray coating a biocompatible film onto a medical device.

Optionally, the biocompatible proteinaceous coating may be spray-applied (a vapor spray coating process). Spray coating provides the advantages of controlled application and uniform coating coverage on the surface. In an embodiment of the invention, two different solutions are sprayed onto the medical device surface at the same time. The first solution comprises a biocompatible coating and linking reagents and the second solution comprises a crosslinker. The biocompatible coating can be tropoelastin and the linking reagents can be those described herein for linking the tropoelastin polypeptides to the silanated device surface. Optionally, a third solution comprising a drug may be sprayed onto the medical device surface contemporaneously with the solution of protein and the solution of crosslinker. FIG. 6 provides a diagram showing a vapor spray coating system that can be used to coat a medical device with a biocompatible coating. In FIG. 6, a medical device 20 is held in place by a holder 22 adjacent to an exhaust system 24. Nebulizers 26, 28, and 30 are supplied with a gas delivery line 32, 34, and 36 (respectively) and a fluid supply line 38, 40, and 42 (respectively). Peristaltic pumps 44, 46, and 48 provide accurate and controlled fluid delivery to the nebulizer heads. Fluid supply lines 38, 40, and 42 are attached to peristaltic pumps 44, 46, and 48 (which can also be an individual peristaltic pump unit capable of accommodating three fluid supply tubes) (respectively), and are fed by three fluid reservoirs 50, 52, and 54 (respectively). Fluid reservoirs 50, 52, and 54 can contain solutions of the biocompatible coating, a crosslinker, and a drug. Mass flow controllers 56, 58, and 60 provide a steady reproducible flow of gas from a gas source (not shown) to the nebulizers 26, 28, and 30 (respectively) create the vapor spray of the biocompatible coating solution, the crosslinker solution, and the drug-containing solution. Typically the gas used will be an inert gas, such as, for example, $N_2$, Ar, or He. The spray coating of the medical device can be accomplished in an inert atmosphere, for example, in a chamber having an inert atmosphere and or by flowing an inert gas sheath around the coating area. Although a relative orientation is shown in FIG. 6 for the components of the vapor coating system, other orientations are possible for the nebulizers and the medical device and may be chosen, for example, to optimize coating uniformity based on device geometry. Additional examples of commercially available devices that may be used to deliver a biocompatible coating as an aerosol spray include the Accu-Mist from Sono-Tek Corporation, Milton, N.Y. The Accu-Mist system has been used for spray-coating stents and other medical devices with drug-eluting polymers. The Accu-Mist creates an atomized spray electrosonically and can be modified to accommodate three spray heads to deliver three different solutions to a medical device.

A SS 316L stent that was subjected to an $O_2$ plasma etch and a solution-based silanation, was coated with tropoelastin monomer using a system as described in FIG. 6. The tropoelastin was crosslinked with disuccinimidyl suberate (DSS) which was sprayed onto the stent contemporaneously with the spray coating of the tropoelastin solution. Unreacted reagents, side products, and molecules other than crosslinked tropoelastin (to the extent these species were present) were removed from the surface by washing the surface. The resulting tropoelastin coating was found to be well adhered using a standard tape test (ASTM D3359) and staining the resulting with mouse anti-rabbit polyclonal antibody against human aortic elastin primary antibody and alexafluor488 secondary antibody and observing the surface with a confocal microscope. The tropoelastin film was found to be without pinholes by testing the coating by digesting it with a guanidine HCl solution and performing XPS analysis to verify the crosslinking reaction. The use of the spray coating method reduced time to coat the stent and improved the uniformity of the coating applied to the stent.

Figure 7:
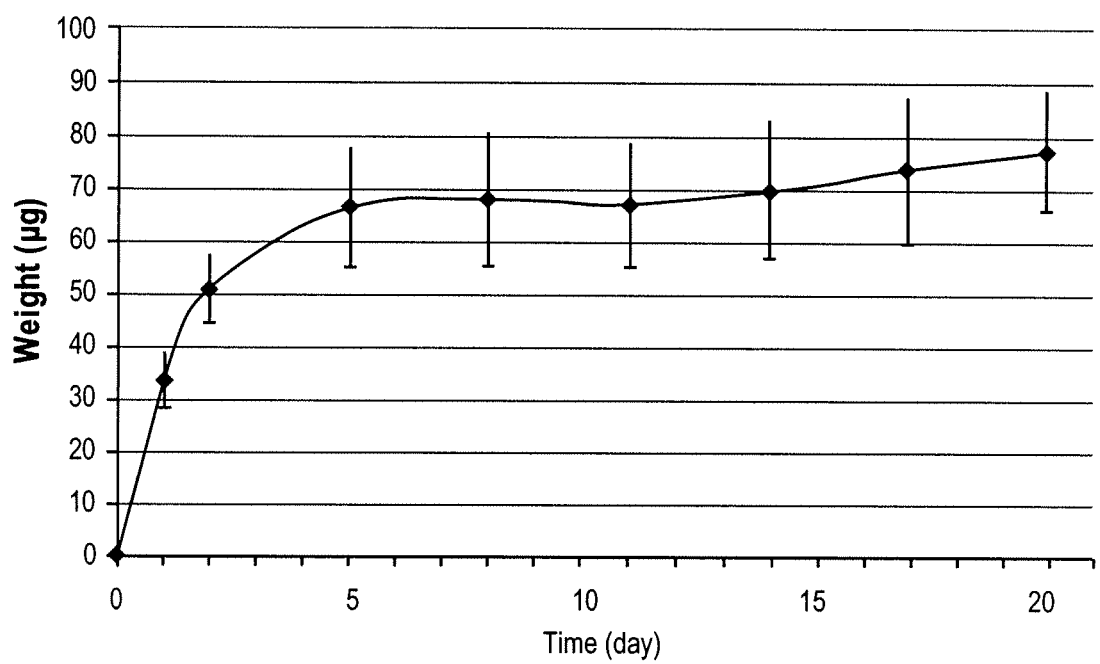
FIG. 7 provides a drug elution profile for a tropoelastin coating containing the drug sirolimus.

The biocompatible coatings of the present invention can optionally be drug-eluting coatings. The addition of a drug to the biocompatible coating can be accomplished, for example, by dip-coating techniques, in which the medical device is dipped into a solution containing the biocompatible coating and the drug to be eluted, and then dipped into a solution containing a crosslinker, or the medical device already having a biocompatible coating is dipped into a solution containing the drug, removed from the solution, and allowed to dry, or the solution containing the drug can be spray-coated onto the medical device, either during the process in which the biocompatible coating is sprayed onto the medical device or after the medical device has already been coated with the biocompatible layer. Excess drug can be eluted from the medical device before deployment. A tropoelastin drug-eluting coating was created. An exemplary drug, sirolimus (rapamycin), was spray coated onto the elastin coated stent using the nebulizer system of FIG. 6. A drug elution profile for the sirolimus from the elastin coating is shown in FIG. 7. The drug density in the tropoelastin coating was about 1 µg/mm$^2$. After 20 days, about 9% of the drug remained in the elastin coating. The elution rate demonstrated by the tropoelastin drug-eluting stent is a useful elution rate for implantable medical devices.

Additional embodiments provide methods for coating an implantable medical device without making physical contact with the device. It is believed that defects in the biocompatible film can arise from methods that require the device to be mechanically held during the coating process, such that only a portion of the device is coated in a first coating process and then the device must be physically repositioned in order for the portion of the device that was masked by the mechanical support to be coated in a second coating process. For example, a stent may be mounted on a rotating mandrel to be coated and after a first coating procedure, manually repositioned to coat the uncoated portion.

Figure 8:
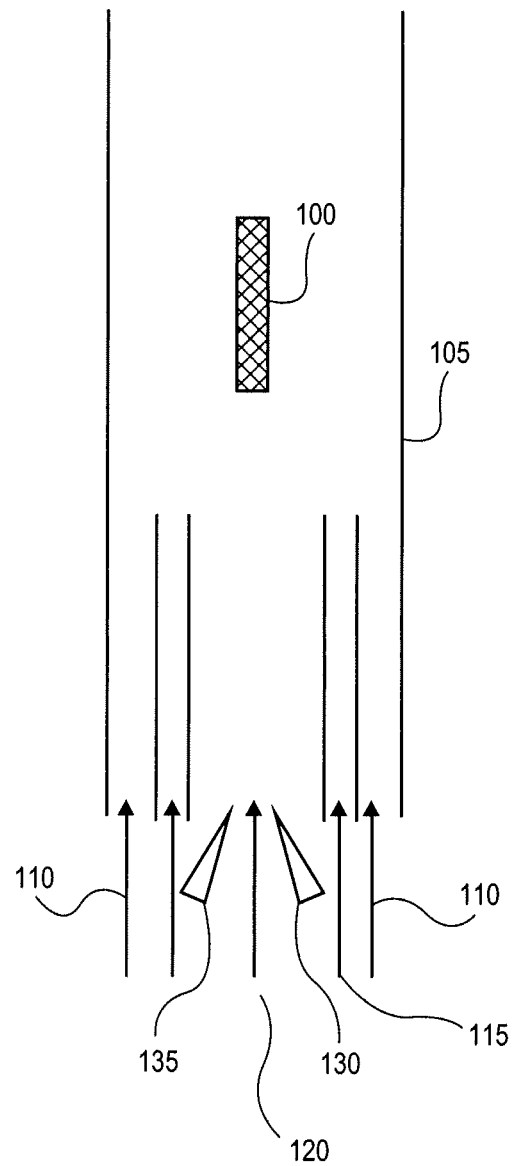
FIG. 8 provides a schematic of an exemplary system for suspending and coating a medical device.

Referring now to FIG. 8, a schematic for a system for coating a medical device is provided. In FIG. 8, a medical device to be coated 100 is suspended and spun in a flowing inert gas in cylindrical chamber 105. Several gas flows are used (indicated by arrows). The outermost gas flow 110 is directed in a manner that creates a vortex that spins the suspended medical device 100. A middle flow 115 between the outer 110 and inner 120 flows is provided. The innermost flow 120 delivers reagents to the device to be coated 100. Reagents include gases for generating a plasma. A plasma is generated, for example, using inductively coupled coils (not shown). Additionally, vaporized silanating agents (as described herein) can be delivered in inert gas flow 120 to the suspended device 100. The device 100 is coated using coating delivery devices 130 and 135 that provide a liquid coating material as a vapor or fine droplet spray (devices such as atomizers, nebulizers, or nozzles, as described herein) for coating the surface of a medical device 100. In this example, medical device 100 is a stent. Additional coating delivery devices may be provided, depending on the number of solutions or coatings to be applied to the surface of the medical device and the method for coating employed. For example, if a coating of tropoelastin and a drug is to be applied, three nozzles can be used: for a tropoelastin solution, for a crosslinker solution, and for a drug containing solution. Alternatively, one or more of the solutions may be mixed before application and applied using one nozzle. Additionally, if the surface of the medical device is to be prepared before the biocompatible coating is applied, such as by the application of a silanating reagent, an additional coating delivery device is used to deliver this reagent to the surface to be coated. Some or all of the solutions could be sprayed at the same time, or individually and or sequentially and or repeatedly to form layers. Because the device is suspended and spun using a flowing gas, no sections of the device to be coated are masked from the coating spray by a surface holding the device. Common inert gases include nitrogen ($N_2$), helium, and argon. The locations and relative geometries of the nozzles can be varied to address considerations such as the size and shape of the device to be coated.

Figure 9:
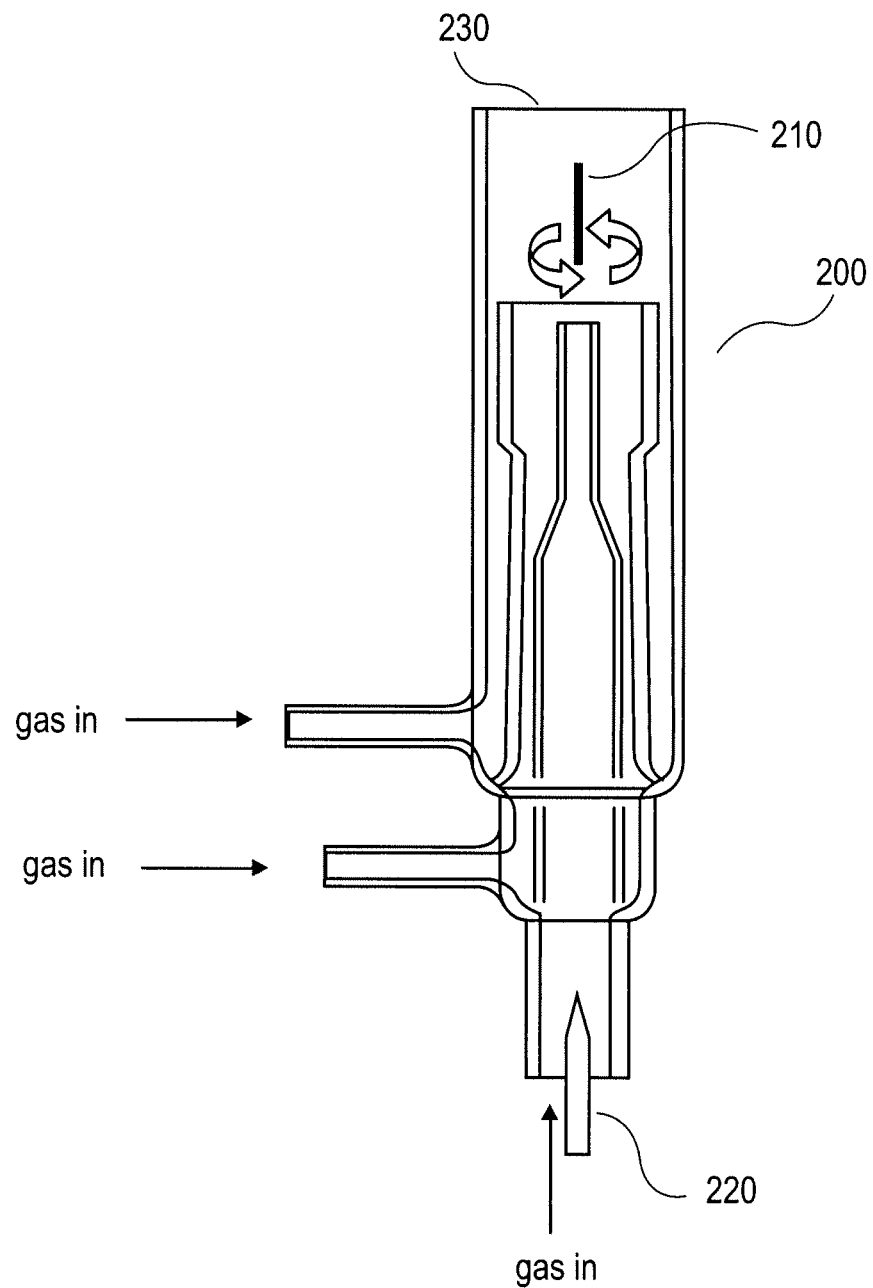
FIG. 9 shows an exemplary device that can be used to coat a medical device suspended in a gas flow.

FIG. 9 provides a drawing of a quartz torch chamber 200 from a standard Inductively Coupled Plasma Mass Spectrometer (ICPMS). In this torch chamber, three flows of an inert gas, such as argon, are used to suspend a medical device 210 and create a vortex that drives the device 210 into the center of the gas. The outermost sheath creates a flow that creates the vortex. An inductively coupled plasma is generated using the RF induction coils (not shown) in the region of medical device 210. Oxygen is provided in the central inert gas stream (flowing upward from the bottom) and the device 210 is etched using an oxygen plasma. A silane layer is created by flowing vaporized silane into the chamber with the central inert gas flow (flowing upward from the bottom). A nebulizer head 220, mounted in the chamber 200 and positioned in the central gas stream (flowing upward from the bottom) delivers coating materials. In the case of forming a coating of tropoelastin and a crosslinker, coating solutions of tropoelastin and crosslinker may be mixed immediately before delivery or two nebulizer heads may be provided. Additionally, a solution containing a drug may applied with the coating, for example, either by mixing the solution with the tropoelastin solution immediately before application, or by providing a second or third nebulizer head. Optionally, coatings such as a tropoelastin coating and a drug coating may be delivered in layers. Waste gases are vented through the exhaust 230. A NirRoyal Gold coated stent was spun and floated in an ICPMS torch using argon gas as illustrated schematically in FIG. 9. From left top to right bottom inlets, gas flow rates were 17 L/min (for the vortex-creating outer sheath), 1 L/min., and 1 L/min. Typical gas flow rates from left top to bottom right inlet are 1-20 l/min., 0-2 L/min., and 0-2 L/min. Because this method does not require physical contact between the device being coated and a support member, the device does not need to be repositioned during the coating process in order to completely cover its surface with coating.

The methods for coating medical devices according to embodiments of the present invention have the additional advantage that the methods are suitable for high volume manufacturing. The plasma processing of the device surface can be accomplished in much less time than the traditional wet chemical approaches (hours as opposed to days). Further the controlled environment used in embodiments of the invention minimizes contamination and provides a more uniform and reproducible bio-compatible coating.

EXAMPLES

Plasma Etch Process: Etching of several SS 316L stainless steel stents was performed on a Plasmalab µEtch 300 from Oxford Instruments. The etch chamber was cleaned before placing the stents in the chamber, using the following parameters for the plasma process: $CF_4$ flow rate set to 60 sccm, $O_2$ set to 25 sccm, set pressure at 400 Torr and forward power set to 500 W for 10 minutes. The chamber was then cleaned using the following parameters for the plasma process: $O_2$ flow rate set to 50 sccm, Ar set to 5 sccm, pressure at 200 Torr, and forward power at 800 W, for 60 minutes. The stents were then placed in the chamber. A 10 second etch was performed using the following parameters: $O_2$ flow rate set to 50 sccm, Ar flow rate set to 5 sccm, set pressure at 200 Torr, forward power set to 800 W. The stents were flipped over and a second etch was performed using the following parameters: $O_2$ flow rate set to 50 sccm, Ar flow rate set to 5 sccm, set pressure at 200 Torr, forward power set to 800 W. Similar processes were used for MP35N stents.

Silanization Reaction: The $O_2$ plasma etch processed SS 316L stainless steel stents were silanized by placing the stents in a solution of 1% APTS by weight in toluene for 24 hours at room temperature. The stents were removed from solution and annealed at 120° C. for 10 minutes in a $N_2$ atmosphere. XPS measurements confirmed silanization as a single layer and the orientation of the amine functional group at the surface of the stent.

Tropoelastin coating: A crosslinked tropoelastin coating was applied to the plasma etch processed and silanized SS 316L stainless steel stents using a set up similar to that described in FIG. 6. A hrTE film was created on the stent by spray coating the stent with a solution containing 12.5 mg/mL hrTE (obtained from Oregon Medical Laser Center (OMLC)) in PBS (phosphate buffered saline, 8 g NaCl, 0.2 g KCl, 1.44 g $Na_2HPO_4$, 0.24 g $KH_2PO_4$ in 800 mL $dH_2O$, pH 7.4) and spraying from a second nebulizer a solution of DSS crosslinker (20 mM DSS in 10% DMSO/PBS (by volume)). The flow rate for the hrTE solution was 20 µL per minute and the flow rate for the DSS solution was 20 µL per minute. The stent was held at the mist-air interface until completely covered with a thin layer of solution (the entire surface was wetted, about 35 minutes) and then allowed to dry. Unreacted reagents, side products, and molecules other than crosslinked tropoelastin were removed from the surface by washing the surface.

Tropoelastin coated SS 316L stents were examined by labeling the tropoelastin with mouse anti-rabbit polyclonal antibody against human aortic elastin primary antibody and alexafluor388 secondary antibody and imaged using a Zeiss Confocal Microscope with magnification 200×. Stents were found to be uniformly coated with a tropoelastin coating.

Drug eluting tropoelastin coating: The drug sirolimus (rapamycin) in a 10 mg/mL solution of ethanol was spray coated on the tropoelastin coated stent using the nebulizer system of FIG. 6. The drug eluting elastin coating was applied in a layering method in which a coating of elastin and DSS was applied, then a coating of elastin, DSS, and drug was applied, and these coatings were repeated twenty times to form sandwich-type layers. The coating process took about 45 minutes and was performed in the presence of a stream of nitrogen gas. Excess drug was removed from the tropoelastin coating by washing the coating surface. The flow rate for the sirolimus solution was 3 µL per minute. The drug density in the tropoelastin coating was found to be 1.02 µg/mm$^2$. FIG. 7 provides a drug elution profile for the drug eluting stent. The stent was placed in a fresh solution of DMSO (dimethylsulfoxide) daily and the DMSO solution was sampled at the end of the day by running an aliquot of the solution on HPLC (High Pressure Liquid Chromatography) and Rampamycin amount was measured (the weight of the Rampamycin was calculated by comparing the absorbance of the stent soaking solution to the absorbance of a standard (known) Rampamycin solution). After 20 days of elution, about 9% of the sirolimus (7.8 µg) remained.

We claim:

1. A method for creating a biocompatible coating comprising:
   providing an object having surface to be coated with a biocompatible film;
   floating the object using a flowing gas wherein the flowing gas comprises a vortex in a region of the flowing gas and wherein the object is rotating about an axis in the flowing gas and wherein the object is located in the vortex; and
   applying a solution comprising a proteinaceous molecule to the surface to be coated under conditions that allow the proteinaceous molecule to coat the surface of the object suspended in a flowing gas.

2. The method of claim 1 wherein the proteinaceous molecule is tropoelastin.

3. The method of claim 2 wherein the proteinaceous molecule is human recombinant tropoelastin.

4. The method of claim 1 wherein the solution comprising a proteinaceous molecule additionally comprises a crosslinker.

5. The method of claim 1 also including applying a solution comprising a crosslinker to the surface to be coated under conditions that allow the crosslinker to coat the surface of the object suspended in a flowing gas.

6. The method of claim 1 wherein the surface to be coated with a biocompatible film is capable of being covalently coupled to a proteinaceous molecule.

7. The method of claim 6 wherein the surface to be coated with a biocompatible film is capable of being covalently coupled to a proteinaceous molecule comprises a silane layer.

8. The method of claim 7 wherein the silane containing layer is capable of being covalently coupled to a proteinaceous molecule through a functional group selected from the group consisting of an amine group, a carboxylic acid group, an aldehyde, an ester, an alkene, an alkyne, a thiol, an isocyanate, a substituted amine, and an alcohol.

9. The method of claim 1 wherein the surface to be coated is the surface of a stent that is capable of being placed in a mammalian blood vessel.

10. The method of claim 4 or 5 wherein crosslinking is accomplished using glutaraldehyde or disuccinimidyl suberate.

11. The method of claim 1 also including aerosolizing a second solution comprising a drug and applying the second aerosolized solution the surface to be coated.

12. The method of claim 11 wherein the drug is selected from the group consisting of antibiotics, immunosuppressive compounds, anti-inflammatories, anti-cell proliferation compounds, anticoagulants, antisense molecules, antivirals, antineoplastics, chemotherapeutics, and combinations thereof.

13. A method for coating a surface with a biocompatible coating comprising:
   providing an object having surface to be coated with a biocompatible film;
   floating the object using a flowing gas wherein the flowing gas comprises a vortex in a region of the flowing gas wherein the object is rotating about an axis in the flowing gas and wherein the object is located in the vortex;
   creating a silane containing layer on the surface of the object suspended in the flowing gas, wherein the silane containing layer is capable of being covalently coupled to a proteinaceous molecule; and
   applying a solution comprising a proteinaceous molecule to the surface of the object suspended in the flowing gas, under conditions that allow the proteinaceous molecule to covalently attach to the surface of the object, wherein the proteinaceous molecule is then covalently coupled to the silane containing layer on the surface of the object.

14. The method of claim 13 also including applying a second solution comprising a crosslinker to the surface of the suspended object.

15. The method of claim 13 wherein the proteinaceous molecule is tropoelastin.

16. The method of claim 13 wherein the proteinaceous molecule is human recombinant tropoelastin.

17. The method of claim 13 wherein the surface to be coated is the surface of a stent that is capable of being placed in a mammalian blood vessel.

18. The method of claim 13 wherein the silane containing layer comprises a functional group selected from the group consisting of an amine group, a carboxylic acid group, an aldehyde, an ester, an alkene, an alkyne, a thiol, an isocyanate, a substituted amine, and an alcohol.

19. The method of claim 13 wherein the silane containing layer is capable of being covalently coupled to a proteinaceous molecule through a carboxylic acid group, an aldehyde, or an ester functional group.

20. The method of claim 13 also including applying a second solution comprising a drug to the surface of the suspended object.

21. The method of claim 20 wherein the drug is selected from the group consisting of antibiotics, immunosuppressive compounds, anti-inflammatories, anti-cell proliferation compounds, anticoagulants, antisense molecules, antivirals, antineoplastics, chemotherapeutics, and combinations thereof.

22. A method for coating a surface with a biocompatible coating comprising:
   providing an object having surface to be coated with a biocompatible film;
   floating the object using a flowing gas wherein the flowing gas comprises a vortex in a region of the flowing gas wherein the object is rotating about an axis in the flowing gas and wherein the object is located in the vortex;
   etching the surface of the suspended object using a plasma process;
   creating a silane containing layer on the surface of the suspended object, wherein the silane containing layer is capable of being covalently coupled to a proteinaceous molecule; and
   applying a solution comprising a proteinaceous molecule to the surface to be coated of the object suspended in the flowing gas, under conditions that allow the proteinaceous molecule to covalently attach to the surface of the object, wherein the proteinaceous molecule is then covalently coupled to the silane containing layer on the surface of the object.

23. The method of claim 22 also including applying a second solution comprising a crosslinker to the surface of the suspended object.

24. The method of claim 22 wherein the proteinaceous molecule is tropoelastin.

25. The method of claim 22 wherein the proteinaceous molecule is human recombinant tropoelastin.

26. The method of claim 22 wherein the silane containing layer is capable of being covalently coupled to a proteinaceous molecule through a carboxylic acid group, an aldehyde, or an ester functional group.

27. The method of claim 22 wherein the surface to be coated is the surface of a stent that is capable of being placed in a mammalian blood vessel.

28. The method of claim 22 also including applying a second solution comprising a drug to the surface of the suspended object.

29. The method of claim 28 wherein the drug is selected from the group consisting of antibiotics, immunosuppressive compounds, anti-inflammatories, anti-cell proliferation compounds, anticoagulants, antisense molecules, antivirals, antineoplastics, chemotherapeutics, and combinations thereof.

* * * * *